(12) United States Patent
Cadwallader et al.

(10) Patent No.: US 9,611,228 B2
(45) Date of Patent: Apr. 4, 2017

(54) STABILIZED COMPOSITIONS AND METHODS OF MANUFACTURE

(71) Applicant: The Board of Trustees of the University of Illinois, Urbana, IL (US)

(72) Inventors: Keith R. Cadwallader, Champaign, IL (US); Ming-Chih Fang, New Taipei (TW)

(73) Assignee: The Board of Trustees of the University of Illinois, Urbana, IL (US)

(*) Notice: Subject to any disclaimer, the term of this patent is extended or adjusted under 35 U.S.C. 154(b) by 158 days.

(21) Appl. No.: 14/210,902

(22) Filed: Mar. 14, 2014

(65) Prior Publication Data

US 2014/0275543 A1 Sep. 18, 2014

Related U.S. Application Data

(60) Provisional application No. 61/787,470, filed on Mar. 15, 2013.

(51) Int. Cl.
| | |
|---|---|
| *C07D 241/12* | (2006.01) |
| *C07D 207/20* | (2006.01) |
| *C07D 211/70* | (2006.01) |
| *C07D 213/50* | (2006.01) |
| *C07D 277/10* | (2006.01) |
| *C07D 277/24* | (2006.01) |

(52) U.S. Cl.
CPC ......... *C07D 241/12* (2013.01); *C07D 207/20* (2013.01); *C07D 211/70* (2013.01); *C07D 213/50* (2013.01); *C07D 277/10* (2013.01); *C07D 277/24* (2013.01)

(58) Field of Classification Search
CPC .................................................. C07D 401/04
See application file for complete search history.

(56) References Cited

U.S. PATENT DOCUMENTS

| | | | |
|---|---|---|---|
| 3,373,177 A | 3/1968 | Young et al. .................... 534/10 |
| 4,522,838 A * | 6/1985 | Buttery ............... A23L 1/22678 |
| | | | 426/537 |
| 5,227,156 A | 7/1993 | Wiese ........................... 514/345 |
| 5,512,290 A | 4/1996 | Duby et al. .................... 424/439 |
| 7,319,181 B2 | 1/2008 | Vanavichit et al. .......... 800/285 |
| 2006/0147596 A1 | 7/2006 | Srinivas et al. ............... 426/534 |
| 2012/0213904 A1 | 8/2012 | Degenhardt et al. ......... 426/537 |

OTHER PUBLICATIONS

Adams, A. and De Kimpe, N. "Chemistry of 2-Acetyl-1-pyrroline, 6-Acetyl-1,2,3,4-tetrahydropyridine, 2-Acetyl-2-thiazoline, and 5-Acetyl-2,3-dihydro-4H-thiazine: Extraordinary Maillard Flavor Compounds" Chemical Review 2006 106:2299-2319.
Apintanapong, M. and Noomhorm, A. "The Use of Spray Drying to Microencapsulate 2-acetyl-1-pyrroline, a Major Flavour Component of Aromatic Rice" International Journal of Food Science and Technology 2003 38:95-102.
Baxter et al. "Stabilisation of 3,4-Dihydro-2H-pyrrole (1-Pyrroline) by Complexation with Zinc Iodide" Synlett 1991 359-360.
Bradbury et al. "The Gene for Fragrance in Rice" Plant Biotechnology Journal 2005 3:363-370.
Buttery et al. "Contribution of Volatiles to Rice Aroma" Journal of Agricultural and Food Chemistry 1988 36:1006-1009.
Erxleben, A. "Structures and Properties of Zn(II) Coordination Polymers" Coordination Chemistry Reviews 2003 246:203-228.
Freer et al. "Structure of Diiodobis(1-pyrroline) zinc(II)" Acta Crystallographica 1993 C49:2115-2117.
Fuhlhage, D.W. and VanderWerf, C.A. "Studies on the Formation and Reactions of 1-Pyrroline" Journal of the American Chemical Society 1958 80:6249-6254.
Kidani et al. "Studies of Bivalent Metal Complexes of 2-Acetylpyridine" Bulletin of the Chemical Society of Japan 1975 48(1):239-244.
Mason, R.B. And Mathews, J.H. "Equilibrium in the Systems: Zinc Chloride-Pyridine; and Cadmium Chloride-Pyridine" Journal of Physical Chemistry 1925 1925:1178-1183.
Schieberle, P. "Quantitation of Important Roast-Smelling Odorants in Popcorn by Stable Isotope Dilution Assays and Model Studies on Flavor Formation During Popping" Journal of Agricultural and Food Chemistry 1995 43:2442-2448.
Singh et al. "Magnetic and Spectroscopic Studies of the Synthesized Metal Complexes of Bis(Pyridine-2-carbo) Hydrazide and Their Antimicrobial Studies" E-Journal of Chemistry 2012 9(4):1835-1842.
Widjaja et al. "Changes in Volatile Components of Paddy, Brown and White Fragrant Rice During Storage" Journal of the Science of Food and Agriculture 1996 71(2):218-224 [Abstract only].

* cited by examiner

*Primary Examiner* — Paul V Ward
(74) *Attorney, Agent, or Firm* — Licata & Tyrrell P.C.

(57) ABSTRACT

A method for stabilization of potent alkanone-heterocyclic flavorants in dry powder form is provided. Coordination of alkanone-heterocyclic flavorants to transition metal salts results in the formation of stable crystalline complexes, which upon hydration release the free flavorant. Food and topping products containing the stabilized alkanone-heterocyclic flavorant are provided as are methods for stabilizing the alkanone-heterocyclic flavorant.

6 Claims, 2 Drawing Sheets

STABILIZED COMPOSITIONS AND METHODS OF MANUFACTURE

INTRODUCTION

This application claims the benefit of priority of U.S. Provisional Application Nos. 61/787,470, filed Mar. 15, 2013, the content of which is incorporated herein by reference in its entirety.

BACKGROUND

2-Acetyl-1-pyrroline (2AP) was first identified in cooked rice (Buttery, et al. (1982) *Chem. Ind.* 12:58-959) and was regarded as the most powerful odorant among all rice volatiles identified (Buttery, et. al. (1983) *J. Agric. Food Chem.* 36:1006-1009). 2AP, with an odor threshold of 0.1 μg/L in water (Buttery, et al. (1982) supra), dominates its homologues 6-acetyl-1,2,3,4-tetrahydropyridine (ATHP, including tautomer 6-acetyl-2,3,4,5-tetrahydropyridine), 2-propionyl-1-pyrroline (2PP), and 2-acetyl-2-thiazoline (2AT), all of which possess roasted, cracker-like, and popcorn-like aroma notes and are also important flavorants in numerous food products (Adams, et al. (2006) *Chem. Rev.* 106:299-2319).

The specialty fragrant or aromatic rice varieties contain high levels of 2AP. In an effort to boost the production of 2AP, the gene linked to the accumulation of 2AP in fragrant rice has been identified (Bradbury, et al. (2005) *Plant Biol. J.* 3:363-370) and transferred into non-aromatic rice varieties, thereby enabling the accumulation of greater levels of 2AP (U.S. Pat. No. 7,319,181). 2AP is of commercial interest to the flavor industry because of its pleasant and characteristic flavor. However, the highly unstable nature of the compound has hindered its widespread commercial use. In popcorn, 2AP decreases by about 80% during room temperature storage for one week in polyethylene bags (Schieberle (1995) *J. Agric. Food Chem.* 43:2442-2448). In raw fragrant rice, the concentration of 2AP was shown to diminish by about half its original content after 3 months (Widjaja, et al. (1996) *J. Sci. Food Agric.* 71:218-224). The instability of 2AP has been postulated to occur via a polymerization reaction (Buttery, et al. (1982) supra). The cyclic imine of 1-pyrroline was shown to form trimers during work-up, which then undergo condensation with neighboring molecules to form polymeric products (Fuhlhage, et al. (1958) *J. Am. Chem. Soc.* 80:6249-6254).

Some efforts have been made to increase the stability of 2AP. For example, a process for encapsulation of 2AP with β-cyclodextrin (β-CD) has been described (U.S. Pat. No. 5,512,290). However, 2AP (10% loading) was decomposed by 91% after 13 days of storage at 20° C. At a loading of 1%, 2AP decomposed by 99% after 110 days of storage. Additional efforts to stabilize 2AP have been suggested through encapsulation, where gum acacia and/or starch are applied to form a stabilized dry powder (US 2006/0147596). However, no proven stability was demonstrated. A crude extract from pandan leaves, a natural source of 2AP, has also been mixed with β-CD to form a powder (US 2012/0213904). However, storage stability data were not reported to demonstrate the effectiveness of this approach. In additional study, 2AP was maintained at a level of 70% after 72 days of storage at ambient temperature when encapsulated at very low loading (0.003%) in a gum acacia/maltodextrin matrix (Apintanapong, et al. (2003) *Int. J. Food Sci. Tech.* 38:95-102).

U.S. Pat. No. 3,373,177 describes metal complexes of β-imino-ketones, which are stable and can be used in fungicides and pesticides, particularly those metals having known toxic effects such as copper, mercury, beryllium and silver. Similarly, U.S. Pat. No. 5,227,156 describes the use of zinc compounds to stabilize a tiazolinone preservative in an anti-dandruff shampoo.

Previous attempts to stabilize 2AP suffer to some extent from at least one of the following deficiencies: 1) stability of 2AP was either not mentioned or was insufficiently studied; 2) low loadings of 2AP were used; and/or 3) 2AP was only stable during storage at low temperature. Therefore, alternative approaches to stabilizing 2AP are needed in the art.

SUMMARY OF THE INVENTION

This invention is a composition comprising, consisting essentially of or consisting of an alkanone-heterocyclic flavorant in complex with a transition metal salt. In some embodiments, the alkanone-heterocyclic flavorant has the structure of Formula I:

Formula I where R is a heterocyclic group and n is 0 to 20. In certain embodiments, the alkanone-heterocyclic flavorant has the structure of Formula II, Formula III or Formula IV:

Formula II

Formula III

Formula IV wherein n is a number from 0 to 20; $R^1$ is N or S; each $R^2$ is independently N, S, C or O; and dashed lines represent a single or double bond, with the proviso that there is either 0 or 1 double bond. In yet other embodiments, the transition metal salt is an iron halide salt, magnesium halide salt, zinc halide salt (e.g., zinc iodide, zinc bromide, or zinc chloride), or a combination thereof. A food product or food topping containing the alkanone-heterocyclic-transition metal salt complex is provided as is a method for stabilizing an alkanone-heterocyclic compound by mixing an alkanone-heterocyclic compound with a transition metal salt in a solvent (e.g., a non-polar solvent).

DETAILED DESCRIPTION OF THE INVENTION

Figure 1:
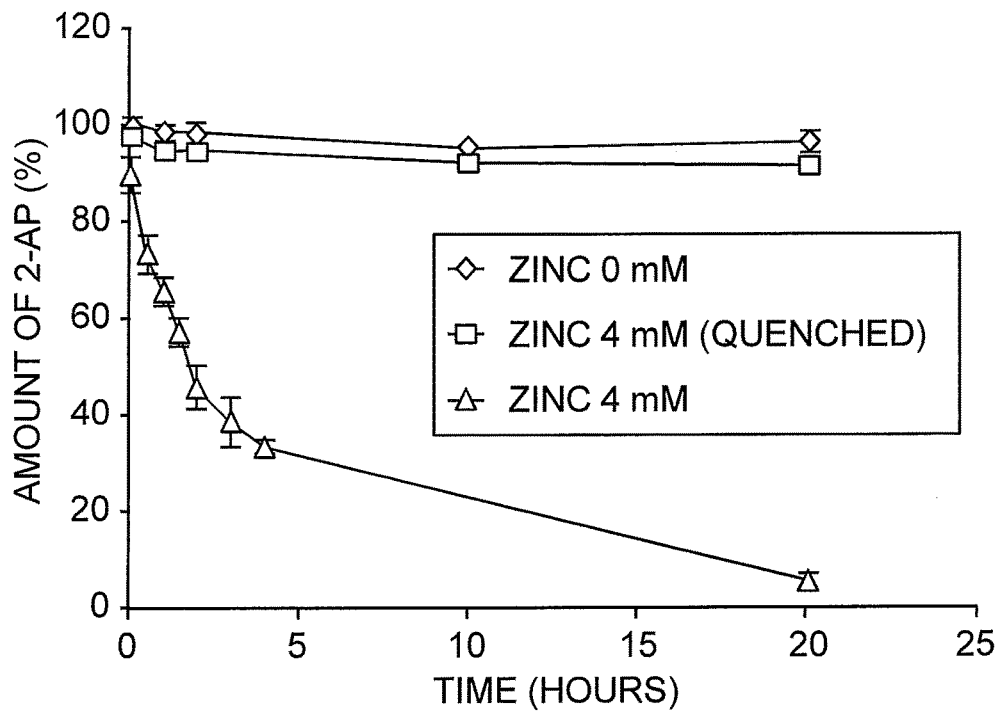
FIG. 1 shows 2-acetyl-1-pyrroline (2-AP) degradation in methylene chloride solution presented zinc iodine (mean±SD, n=2).

It has now been found that complexation of unstable alkanone-heterocyclic flavorants with transition metal salts, such as zinc halides, forms a solid complex in powder form, which is stable at ambient temperature, e.g., only 6% reduction during a 3 months of storage at 25° C. Therefore, this invention is a stabilized composition containing an alkanone-heterocyclic-transition metal salt complex, methods for preparing the complex and methods of using the complex to flavor food products and topping products.

As used herein, an alkanone-heterocyclic flavorant of the alkanone-heterocyclic-transition metal salt complex has the structure A-R, wherein A is an alkanone group and R is a heterocyclic group.

As used herein, an alkanone is a group having a carbonyl group linked to a carbon atom in each of two hydrocarbon radicals. In certain embodiments, the alkanone of this invention has the structure:

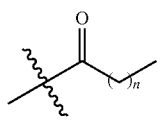

where n is a number from 0 to 20. In some embodiments, n is 0 to 10, 0 to 5, 0 to 4, 0 to 3, 0 to 2, or 0 to 1. In some embodiments, the alkanone is a propionyl group. In other embodiments, the alkanone is an acetyl group.

For the purposes of this invention, a heterocyclic group is a saturated or partially unsaturated monovalent monocyclic group of 4 to 8 ring atoms in which one, two, or three ring atoms are heteroatoms independently selected from the group of N, O, or S and the remaining ring atoms are C. Unless otherwise stated, the valency of the group may be located on any atom of any ring within the radical, valency rules permitting. In some embodiments, the heterocyclic group is a saturated heterocyclic group such an azetidinyl, oxetanyl, thietanyl, pyrrolidinyl, oxolanyl, thiolanyl, piperidinyl, oxanyl, thianyl, thiazolidinyl, oxazolidinyl, oxathiolanyl, oxazinanyl, thiazinanyl, or oxathianyl. In other embodiments, the heterocyclic group is a partially unsaturated heterocyclic group such as azetyl, oxetyl, thietyl, pyrrolyl, furanyl, thiophenyl, pyridinyl, pyrazinyl, pyranyl, thiopyranyl, tetrahydropyridinyl, dihydrothiopyranyl, and dihydropyranyl. A heterocyclic group of the invention can be unsubstituted or substituted with one or more alkyl, alkenyl, aryl, halo, hydroxyl, oxo, amino, amido, or cyano groups, which can optionally substituted.

As used herein an alkyl group is a straight-chain, branched or cyclic alkyl group. Alkyl groups include those having from 1-20 carbon atoms. Alkyl groups include small alkyl groups having 1-3 carbon atoms. Alkyl groups include medium length alkyl groups having from 4-10 carbon atoms. Alkyl groups include long alkyl groups having more than 10 carbon atoms, particularly those having 10-20 carbon atoms. Cyclic alkyl groups include those having one or more rings. Cyclic alkyl groups include those having a 3-, 4-, 5-, 6-, 7-, 8-, 9- or 10-member carbon ring and particularly those having a 3-, 4-, 5-, 6-, or 7-member ring. The carbon rings in cyclic alkyl groups can also carry alkyl groups. Cyclic alkyl groups can include bicyclic and tricyclic alkyl groups. Alkyl groups optionally include substituted alkyl groups. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2-20 carbon atoms. Alkenyl groups include small alkyl groups having 2-3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cyclic alkenyl groups include those having one or more rings. Cyclic alkenyl groups include those in which a double bond is in the ring or in an alkenyl group attached to a ring. Cyclic alkenyl groups include those having a 3-, 4-, 5-, 6-, 7-, 8-, 9- or 10-member carbon ring and particularly those having a 3-, 4-, 5-, 6- or 7-member ring. The carbon rings in cyclic alkenyl groups can also carry alkyl groups. Cyclic alkenyl groups can include bicyclic and tricyclic alkyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted.

Aryl groups include groups having one or more 5- or 6-member aromatic or heteroaromatic rings. Aryl groups can contain one or more fused aromatic rings. Aryl groups are optionally substituted. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted.

In certain embodiments, the heterocyclic group of the alkanone-heterocyclic-transition metal salt complex of this invention has one of the following structures:

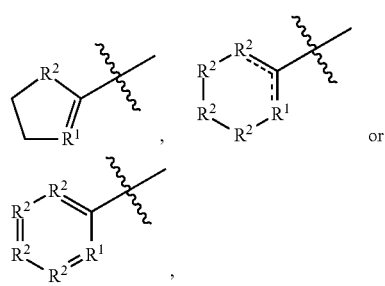

wherein $R^1$ is N or S; each $R^2$ is independently N, S, C or O; and dashed lines represent a single or double bond, with the proviso that there is either 0 or 1 double bond in the heterocyclic group. Unless stated otherwise, the heterocyclic group is unsubstituted or may be substituted with one, two, or three ring system substituents which may be the same or different.

In some embodiments, the alkanone-heterocyclic flavorant of the instant complex is represented by the Formula I:

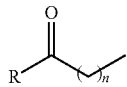

Formula I where R is a heterocyclic group as defined herein and n is a number from 0 to 20. In certain embodiments, a compound of Formula I is more specifically represented by a compound of Formula II, Formula III or Formula IV:

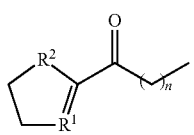

Formula II

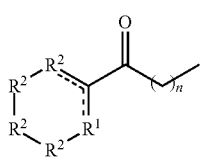

Formula III

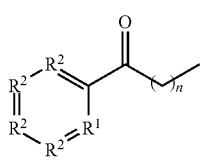

Formula IV wherein n is a number from 0 to 20; $R^1$ is N or S; each $R^2$ is independently N, S, C or O; and dashed lines represent a single or double bond, with the proviso that there is either 0 or 1 double bond.

Exemplary alkanone-heterocyclic flavorants include the following:

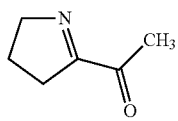 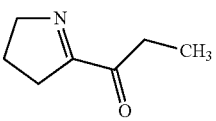

2-acetyl-1-pyrroline (2AP)   2-propionyl-1-pyrroline (2PP)

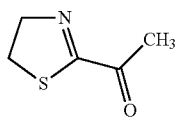 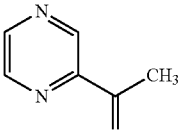

2-acetyl-2-thiazoline (2A2T)   2-acetylpyrazine (2APry)

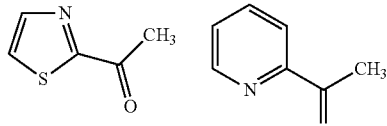

2-acetylthiazole (2ATz)   2-acetylpyridine (2APri)

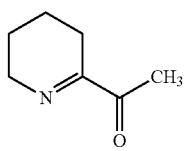

6-acetyl-1,2,3,4-tetraphydopyridine and its tautomer 6-acetyl-2,3,4,5-tetrahydropyridine (ATHP).

As indicated, the present invention provides stabilized alkanone-heterocyclic flavorants via complexation of the alkanone-heterocyclic flavorant with transition metal salts. In some embodiments, the metal is in period 3 or 4 of the periodic table and/or group 2 to 12 of the period table. In certain embodiments, the transition metal is iron (Fe), magnesium (Mg), or zinc (Zn) and the associated counter ion is a halide, such as chloride (Cl⁻), bromide (Br⁻), or iodide (I⁻). Thus, in some embodiments, the transition metal salt is an iron halide salt, magnesium halide salt or zinc halide salt. In particular embodiments, the transition metal salt is a zinc halide salt. Exemplary, transition metal salts include, but are not limited to, $FeCl_2$, $ZnCl_2$, $ZnBr_2$, $MgCl_2$, and $ZnI_2$. Conjugate bases of organic acids are also included within the scope of this invention. In particular embodiments, the transition metal salt is Generally Recognized As Safe (GRAS) for use in food products.

The alkanone-heterocyclic-transition metal salt complex of this invention is prepared by combining or mixing an anhydrous alkanone-heterocyclic flavorant with a transition metal salt in a solvent, in particular a non-polar solvent. A non-polar solvent is a solvent with a dielectric constant of less than 15. Non-polar solvents include, e.g., pentane, cyclopentane, hexane, cyclohexane, benzene, toluene, 1,4-dioxane, chloroform and diethyl ether. In general, a temperatures between about −20° C. to 30° C.; between about −20° C. and 5° C.; between about −20° C. and 0° C. can be used for complexation. Once the alkanone-heterocyclic-transition metal salt complex is formed, e.g., as evidenced by the formation of a precipitate, the complex can be washed (e.g., with a non-polar solvent) and solvent can be removed, e.g., by purging with nitrogen. In certain embodiment, the alkanone-heterocyclic-transition metal salt complex composition is provided in powder form.

Given the roasted, cracker-like, and popcorn-like aroma notes provided by the alkanone-heterocyclic flavorants described herein, the stabilized alkanone-heterocyclic-transition metal salt complex of this invention finds application as a flavorant or additive of a food product or food toppings. The term "flavorant" refers to an ingredient used to impart aroma and/or flavor to a product. The alkanone-heterocyclic-transition metal salt complex of this invention can be added to a food product or topping product in relatively small amounts, e.g., in range of 1 gram to 100 grams of flavorant to 1 ton of food or topping product.

In particular embodiments, the alkanone-heterocyclic-transition metal salt complex is a flavorant or additive of a dry food or topping product, wherein upon hydration, the alkanone-heterocyclic flavorant is released from the transition metal salt complex to impart aroma and/or flavor to the product. Dry food or food products include, but are not limited to oven baked food products, deep fried crisps, extruded products, dry roasted nuts, toasted products and general dry food products, e.g., dry food products made of wheat, corn, potato, rice and mixtures thereof. Oven baked food products include, e.g., biscuits, cookies, pretzels, toasts, crackers, and snacks. Toppings for the purpose of the present invention include dry blended flavorings, seasonings, decorations, and mixtures thereof. In some embodiments, the alkanone-heterocyclic-transition metal salt complex is combined with edible oils, lipids and/or waxes to enhance the stabilization effect of the complex and/or to impart desired flavor, aroma, and/or processing characteristics to the food product.

The invention is described in greater detail by the following non-limiting examples.

EXAMPLE 1

Material and Methods

Chemicals. 2-Acetyl-2-thiazoline (2A2T), 2-acetylthiazole (2ATz), 2-acetylpyridine (2APri), 2-acetylpyrazine (2APry), piperidine, pyrrolidine, 2-acetylpyrrole, collidine, nonane, zinc chloride (1.0 M solution in diethyl ether), zinc bromide, iodomethane, bromoethane, magnesium (turnings, ~⅛ inch), zinc (dust, <10 µm), iodine, boric acid and zircon monosodium salt were purchased from Sigma-Aldrich (St Louis, Mo.). 2A2T was purified by removing impurities via anhydrous diethyl ether, and by subsequent distillation in vacuo. Zinc iodide was prepared by stirring zinc and iodine in anhydrous diethyl ether for 3 days. Anhydrous diethyl ether and methylene chloride were obtained from Fisher Scientific (Fair Lawn, N.J.). 2AP (yield=10% from pyrrolidine; purity=91%) and ATHP (yield=5% from piperidine; purity=83% with two tautomers 6-acetyl-1,2,3,4-tetrahydropyridine and 6-acetyl-2,3,4,5-tetrahydropyridine at a ratio of 7:3) were synthesized according to established methods (De Kimpe, et al. (1993) *J. Agric. Food Chem.* 41:1458-1461; De Kimpe, et al. (1993) *J. Org. Chem.* 58:2904-2906). 2-Propionyl-1-pyrroline was prepared by reacting 2-cyano-1-pyrroline with ethylmagnesium bromide in diethyl ether, by following closely the published procedure for the synthesis of 2-acetyl-1-pyrroline (yield=4% from pyrrolidine; purity=42%). 2-Ethyl-1-pyrroline was synthesis as described in the art (Fuganti, et al. (2007) *Tetrahedron.* 63:4762-4767).

General Procedure for the Preparation of Alkanone-Heterocyclic Compound-Zinc Halide Complexes.

An anhydrous etheric solution of 2AP or other alkanone-heterocyclic compound (1 mmol in 10 mL ether) was added to dry zinc iodide, zinc bromide or zinc chloride in anhydrous diethyl ether (0.1M) in a 50-mL centrifuge tube with stirring and nitrogen purging. During addition, a significant amount of precipitate was observed. The reaction mixture was stored at −20° C. for 5 minutes, and then centrifuged (3000×g, 3 minutes). The precipitate was washed with fresh anhydrous diethyl ether (10 mL×3), and then collected. Solvent was removed by gentle purging with nitrogen to obtain a fine powdered complex, which was stored at −20° C. in a vial equipped with a polytetrafluoroethylene (PTFE)-lined silicon cap.

Quantitation of Alkanone-Heterocyclic Compound Content of Complexes.

Complex (5-10 mg) was placed in a 1.5 mL vial, and 0.5 mL of aqueous phosphate buffer (50 mM, pH 7) was subsequently added (this solution turned cloudy/white because of the insoluble metal content). Subsequent extraction was conducted via addition of methylene chloride (0.5 mL) containing an internal standard (collidine, 1.00 mg/mL). This mixture was vigorously shaken by hand for 1 minute, and then centrifuged (3000×g, 5 minutes). The solvent layer was recovered and dried over sodium sulfate prior to gas chromatography (GC) analysis. Authentic standard alkanone-heterocyclic compounds were dissolved in phosphate buffer and extracted with methylene chloride following the above procedure to generate response factors for each alkanone-heterocyclic compound against the internal standard. The content of an alkanone-heterocyclic compound in a complex was calculated using the following equation:

Loading (%)=area of alkanone-heterocyclic compound peak/area of collidine peak concentration of collidine (mg/mL)×0.5 mL×response factor/sample weight (mg)×100%.

Stability of 2AP with Zn Iodide in Solution.

2AP (2000 µg/mL) in pentane (1 mL) and zinc iodide diethyl ether solution (0.2 M, 0.2 mL) were combined with 8 mL of methylene chloride (containing nonane as internal standard at 1.00 mg/mL) in a 10-mL volumetric flask and the volume immediately made up to the mark with methylene chloride. The solution was incubated at room temperature for a period of 20 hours during which time the 2AP content was periodically monitored by transferring a 0.5 mL aliquot of the sample solution into a 1.5 mL vial followed by addition of a 0.5 mL quenching solution (phosphate buffer, 50 mM, pH 7). The mixture was shaken and centrifuged (3000×g, 5 minutes) and the solvent layer was immediately analyzed by GC. To check the stability of the quenched 2AP extract, the initial sample (time zero, quenched immediately after zinc iodide addition) was held at room temperature and analyzed periodically by GC for up to 20 hours. To serve as a control, a separate 2-AP solution, which did not contain zinc iodide, was also stored at room temperature and monitored periodically during this same time period.

Gas Chromatography.

Gas chromatography was performed using either a 6890N GC/5973N mass selective detector (MSD; Agilent Technologies Inc., Palo Alto, Calif.) equipped with a fused-silica capillary column (STABILWAX, 30 m×0.25 mm×0.25 µm film thickness, or RTX-5, 15 m×0.32 mm×0.5 µm film thickness; Restek, Bellefonte, Pa.); or a 5890 series II GC equipped with a split/splitless injector, flame ionization detector (FID) and HP-1 column (30 m×0.32 mm×0.25 µm film thickness; Agilent). Helium was the carrier at a constant flow of 1 mL/minute. The injector was held at 250° C. in the split mode. GC oven temperature was programmed from 50 to 225° C. at 10° C./minute with initial and final hold times of 5 and 20 minutes, respectively. Other conditions for the MSD were as follows: MSD interface temperature, 260° C.; ionization energy, 70 eV; mass range, 35-350 amu; EM voltage, Autotune+165 V; scan rate, 4.45 scans/second.

Determination of Zinc Content in Alkanone-Heterocyclic Compound-Zinc Complexes.

Zinc content was measured spectrophotometrically according to known methods (Säbel, et al. (2010) *Anal. Biochem.* 397:218-226). Samples (5 to 10 mg) were diluted in water (pH 2, adjusted using HCl) in a 25-mL volumetric flask. A 70 µL aliquot of this solution, plus 100 µL of Zincon dye (1.6 mM; 37 mg Zincon in 1 mL NaOH (1M) prior to dilute into 50 mL water) and 3 mL borate buffer (53 mM, pH 9.0), were combined in a test tube. After incubation of this solution for 5 minutes, absorbance was measured at 620 nm using a Lambda 1050 UV/VIS/NIR spectrophotometer (PerkinElmer Inc., Shelton, Conn.). A six-point calibration plot was constructed from a dilution series of a zinc stock solution (100 mg zinc dust in 1 mL HCl for 4 hours prior to dilution to 1 L).

Infrared Spectra.

Infrared spectra of the alkanone-heterocyclic compounds and their zinc halide complexes were recorded using SPECTRUM 100 FT-IR (PerkinElmer Inc.) with Attenuated Total Reflectance (ATR) accessory (Resolution=cm$^{-1}$, 4 scans/spectra, range=500 cm$^{-1}$~4000 cm$^{-1}$). Liquid Samples were analyzed in neat form. Solid complexes were applied directly to the diamond ATR top-plate.

Stability of 2AP Zinc Iodide Complex in Dry Powder Form.

2AP zinc iodide complex (5 to 10 mg) was stored in sealed (PTFE-lined silicon cap) 1.5-mL glass vials and stored at 25° C., 10° C. or −20° C. in a desiccator under vacuum and in presence of desiccant (calcium chloride). The residual 2AP in complex was monitored during a 3 month storage period as previously described.

EXAMPLE 2

Complexation of Alkanone-Heterocyclic Compounds to Zinc Halide

The addition of anhydrous zinc iodide to a dry solution of 2AP in diethyl ether caused a yellowish precipitate to form immediately. This reaction mixture was incubated in the freezer for 5 minutes, and then triturated with fresh anhydrous diethyl ether to remove excess zinc iodide and other impurities from the 2AP-zinc iodide complex. A fine powder, pale-yellow in color, was obtained after collecting the precipitate and purging with nitrogen. The free 2AP ligand could be freed from the powdered 2AP-zinc iodide complex via hydration with water, in which case a white cloudy metallic substance also appeared at neutral pH and the yellow color faded immediately. GC-MS analysis of a methylene chloride extract of this aqueous mixture yielded a single peak with a mass spectrum and retention index closely matching those of authentic 2AP.

The 2AP-zinc iodide complex acts to stabilize 2AP through the coordination of the ring nitrogen and carbonyl oxygen atoms of the compound to the zinc ion. Coordination of 2AP with other zinc salts such as zinc bromide and zinc chloride acts in a similar fashion; however, during the preparation of the 2AP-zinc chloride complex, a white sticky precipitate formed initially and later a hard layer formed. This reaction mixture was centrifuged and then triturated with fresh anhydrous diethyl ether during which the sticky precipitate was converted into a powder. In the case of zinc chloride complex the trituration step prevented transformation of the complex into a red viscous material, which likely results from the polymerization of 2AP. This same phenomenon occurred in the preparation of the 2-PP-zinc iodide, 2-PP-zinc bromide and 2-PP-zinc chloride complexes and for the 2-ethyl-1-pyrroline-zinc iodide complex, but was not observed for the other alkanone-heterocyclic compound-zinc halide complexes. Yields and color of the resulting alkanone-heterocyclic compounds-zinc halide complexes are provided in Table 1.

TABLE 1

| Complex | Yield[a] | Color |
|---|---|---|
| ZnI$_2$(2AP)$_n$ | 62% | pale yellow |
| ZnBr$_2$(2AP)$_n$ | 96% | white |
| ZnCl$_2$(2AP)$_n$ | 86% | white |
| ZnI$_2$(2PP)$_n$ | 32% | orange |
| ZnBr$_2$(2PP)$_n$ | 49% | pale yellow |
| ZnCl$_2$(2PP)$_n$ | 60% | pale yellow |
| ZnI$_2$(2A2T)$_n$ | 90% | yellow |
| ZnBr$_2$(2A2T)$_n$ | 95% | white |
| ZnCl$_2$(2A2T)$_n$ | 98% | Pale yellow |
| ZnI$_2$(ATHP)$_n$[b] | 59% | yellow |
| ZnBr$_2$(ATHP)$_n$ | 71% | pale yellow |
| ZnCl$_2$(ATHP)$_n$ | 100% | pale yellow |
| ZnI$_2$(2APri)$_n$ | 102% | white |
| ZnBr$_2$(2APri)$_n$ | 97% | white |
| ZnCl$_2$(2APri)$_n$ | 101% | white |
| ZnI$_2$(2APry)$_n$ | 74% | orange |
| ZnBr$_2$(2APry)$_n$ | 93% | white |
| ZnCl$_2$(2APry)$_n$ | 91% | white |
| ZnI$_2$(2ATz)$_n$ | 40% | pale yellow |
| ZnBr$_2$(2ATz)$_n$ | 76% | white |
| ZnCl$_2$(2ATz)$_n$ | 103% | white |

[a] Yield = W/(mM × MW ÷ n) × 100% [W = amount (mg) of obtained complex; mM = amount (mM) of starting alkanone-heterocyclic; MW = molecular weight of complex (based on the formula in this table)].
[b] ATHP, 2-acetyl-3,4,5,6-tetrahydropyridine and its tautomer 2-acetyl-1,4,5,6-tetrahydropyridine.

EXAMPLE 3

Stoichiometry of Complex Formation

Contents of alkanone-heterocyclic compounds and zinc metal in the various complexes were determined by GC and spectrophotometric analyses, respectively. The theoretical loadings of 2AP were 26%, 33%, and 45% in the zinc iodide, zinc bromide and zinc chloride complexes, respectively. However, it was found that the content of 2AP was, respectively, only 12-17%, 11%, 13% in the zinc iodine, zinc bromide, and zinc chloride complexes. The lower loadings could be due to the instability of 2AP which may have degraded during the complexation step. Similar phenomena were observed for the complexes of 2PP and ATHP, which are both unstable cyclic imines. Table 2 shows the proposed stoichiometry and content analysis of 21 alkanone-heterocyclic-zinc halide complexes. 2A2T, APri, APra, and ATz had values close to their calculated alkanone-heterocyclic compound and metal contents. For 2AP, 2PP, and ATHP, only the zinc contents were used for the determination of their proposed stoichiometry, due to the poor recovery of the alkanone-heterocyclic compounds.

TABLE 2

| | | Found (calcd.) (%, n = 2, mean ± SD) | |
|---|---|---|---|
| Complex | Stoichiometry[a] (n) | Heterocyclic | Zinc Halide |
| ZnI$_2$(2AP)$_n$ | 1 | 17 ± 2 (26) | 73 ± 2 (74) |
| ZnBr$_2$(2AP)$_n$ | 1 | 11 ± 1 (33) | 67 ± 2 (67) |
| ZnCl$_2$(2AP)$_n$ | 1 | 13 ± 1 (45) | 57 ± 13 (55) |
| ZnI$_2$(2PP)$_n$ | 1 | 8 ± 1 (28) | 76 ± 2 (72) |
| ZnBr$_2$(2PP)$_n$ | 1 | 13 ± 1 (36) | 65 ± 5 (64) |
| ZnCl$_2$(2PP)$_n$ | 1 | 23 ± 2 (48) | 53 ± 3 (52) |
| ZnI$_2$(2A2T)$_n$ | 2/3 | 25 ± 2 (21) | 77 ± 5 (79) |
| ZnBr$_2$(2A2T)$_n$ | 2/3 | 33 ± 1 (28) | 72 ± 2 (72) |
| ZnCl$_2$(2A2T)$_n$ | 2/3 | 47 ± 11 (39) | 61 ± 2 (61) |
| ZnI$_2$(ATHP)$_n$[b] | 1 | 7 ± 1 (28) | 71 ± 11 (72) |
| ZnBr$_2$(ATHP)$_n$ | 1 | 10 ± 0 (36) | 68 ± 1 (64) |
| ZnCl$_2$(ATHP)$_n$ | 1 | 25 ± 2 (48) | 56 ± 6 (52) |

TABLE 2-continued

| Complex | Stoichiometry[a] (n) | Found (calcd.) (%, n = 2, mean ± SD) | |
|---|---|---|---|
| | | Heterocyclic | Zinc Halide |
| $ZnI_2(2APri)_n$ | 2 | 42 ± 2 (43) | 59 ± 1 (57) |
| $ZnBr_2(2APri)_n$ | 2 | 52 ± 2 (52) | 51 ± 7 (48) |
| $ZnCl_2(2APri)_n$ | 2 | 58 ± 2 (64) | 36 ± 0 (36) |
| $ZnI_2(2APry)_n$ | 2/3 | 25 ± 0 (20) | 79 ± 8 (80) |
| $ZnBr_2(2APry)_n$ | 2/3 | 30 ± 2 (27) | 73 ± 1 (73) |
| $ZnCl_2(2APry)_n$ | 2/3 | 37 ± 1 (37) | 65 ± 5 (63) |
| $ZnI_2(2ATz)_n$ | 1 | 27 ± 0 (29) | 72 ± 1 (72) |
| $ZnBr_2(2ATz)_n$ | 1 | 36 ± 0 (36) | 64 ± 1 (64) |
| $ZnCl_2(2ATz)_n$ | 1 | 47 ± 2 (48) | 54 ± 1 (52) |

[a]Proposed stoichiometry.
[b]ATHP, 2-acetyl-3,4,5,6-tetrahydropyridine and its tautomer 2-acetyl-1,4,5,6-tetrahydropyridine.

Zinc halide is postulated to have two binding sites in its complex (Baxter, et al. (1991) *Synlett.* 359-360). However, due to its flexible coordination, four or even six chelate rings have also been reported (Erxleben (2003) *Cood. Chem. Rev.* 203-228). Because 2AP, 2PP and ATHP contained two donors atoms (a nitrogen and a carbonyl oxygen), they were postulated to form 1-to-1 metal-ligand complexes. However, although APri contained two donors as well, it has been found to form bivalent metal complexes (Kidani, et al. (1975) *Bull. Chem. Soc. Jap.* 48:239-244) and, accordingly, the APri-zinc complexes were found to have four binding sites. 2AT and APra were believed to form $(ZnX_2)_3L_2$ complexes (where, X=I, Br or Cl; L=APra ligands) since both had three possible donor sites (nitrogen, carbonyl, and sulfur atoms (Weaver, et al. (1970) *Inorg. Chem.* 9:268-273) for 2-AT; two nitrogens and a carbonyl for APra). However, the same rule did not apply to ATz, for which 1-to-1 complexes were found even though ATz contains three donor atoms. The same ligands or structurally similar ligands that link to zinc halide may have various coordinations. For example, pyrazine zinc bromide may yield two reversible coordination polymers, pyrazine-$ZnBr_2$, which forms zigzag chain polymer with a tetrahedral center, and (pyrazine)$_2$-$ZnBr_2$, which forms 2D regular square-grid network with octahedral center (Bourne, et al. (2001) *J. Chem. Soc. Dalton Trans.* 1176-1179).

EXAMPLE 4

Infrared Spectra and Nature of Coordination

The infrared spectra of the Zn(II)-heterocyclic complexes were recorded in the range of 4000-400 $cm^{-1}$, but only 2000-600 $cm^{-1}$ region was considered. The carbonyl (C═O) band assignments for the complexes are given in Table 3.

TABLE 3

| | Carbonyl Vibration ($cm^{-1}$) | | | | |
|---|---|---|---|---|---|
| Compound | Free ligand | $ZnI_2$ Complex | $ZnBr_2$ Complex | $ZnCl_2$ Complex | Peak shape |
| 2AP | 1695 | 1627 | 1630 | 1633 | broadened, split |
| 2PP | 1698 | 1647 | 1640 | 1642 | |
| ATHP | 1695, 1666 | 1632 | 1635 | 1637 | |
| 2AT | 1700 | 1694 | 1696 | 1702 | broadened, split |
| 2ATz | 1682 | 1656 | 1654 | 1655 | |

TABLE 3-continued

| | Carbonyl Vibration ($cm^{-1}$) | | | | |
|---|---|---|---|---|---|
| Compound | Free ligand | $ZnI_2$ Complex | $ZnBr_2$ Complex | $ZnCl_2$ Complex | Peak shape |
| 2APry | 1688 | 1674 | 1673 | 1675 | split |
| 2APri | 1696 | 5659 | 1672 | 1676 | split |

It was observed that the carbonyl vibration shifted to lower wave numbers for the complexes as compared to their free ligands, indicating the existence of a coordination complex. This was observed for all complexes except for those of 2A2T. For example, 2AP produced a very strong absorption around 1695 $cm^{-1}$, which was attributed to C═O stretching. The corresponding bands shifted to the lower wave numbers at 1627 $cm^{-1}$, 1630 $cm^{-1}$, and 1633 $cm^{-1}$, for its zinc iodide, zinc bromide, and zinc chloride complexes, respectively. This provides evidence for coordination through the carbonyl oxygen. In addition, the broadened band width at around 1695 $cm^{-1}$ in the complexes may be considered as further evidence for metal chelation (Singh, et al. (2002) *e-J. Chem.* 9:1835-1842). The heterocyclic ring nitrogen was suggested to undergo bond formation with the metal, thus increasing the dipolar contribution of C═N[+] (Kidani, et al. (1975) supra). Bands at 1632 $cm^{-1}$ or 1619 $cm^{-1}$ may be assigned as ring nitrogen vibration. However, the C—C vibration occurred at around 1600 to 1650 $cm^{-1}$ with broad and split or multi-peak shapes, which always overlapped the nitrogen (C–N═C) region thereby making it more difficult to determine the coordination between the metal and ring nitrogen. It is believed that nitrogen was involved in coordination because many heterocyclic-metal complexes containing only nitrogen and carbon have been previously observed, such as (1-pyrroline)2-zinc iodide (Baxter, et al. (1991) supra), (pyridine)2-zinc chloride, (pyridine)6-cadmium chloride (Mason, et al. (1925) *J. Phys. Chem.* 1925:1178-1183), pyrazine-zinc bromide (Bourne, et al. (2001) supra), and (2-ethyl-1-pyrroline)2-zinc iodide.

For ATHP, the carbonyl vibration located at 1695 $cm^{-1}$ and 1666 $cm^{-1}$ in the free ligand, disappeared upon O-complexation, and shifted to lower wave numbers of 1632 $cm^{-1}$, 1635 $cm^{-1}$, and 1637 $cm^{-1}$ in its zinc iodide, zinc bromide, and zinc chloride complexes, respectively. The two bands for ATHP indicated the carbonyl groups of two tautomers. However, there was only one band observed in their complexes, which suggested a single stable ATHP-zinc halide complex was constructed. However, for 2A2T complexes, the differences between coordinated and non-coordinated carbonyl groups was evidenced by only the broadening and splitting of this band which was located at around 1700 $cm^{-1}$. A strong C═N stretching band at 1592 $cm^{-1}$ (Doornbos, et al. (1972) *Recl. Trav. Chim. Pay-Bas.* 91:711-728) shifted to lower wave numbers at 1574 $cm^{-1}$, 1576 $cm^{-1}$, 1576 $cm^{-1}$ for its zinc iodide, zinc bromide, and zinc chloride complexes, respectively, apparently indicating N coordination.

EXAMPLE 5

Unstable Nature of 2AP

Lower loadings were observed in the complexes of 2AP, as well in 2PP and ATHP. This could be due to the instability of imines, which decayed to some extent during complexation. It was observed that 2AP zinc iodide complex solutions prepared in methanol, acetone, dimethyl sulfoxide (DMSO), propylene glycol, or glycerin turned red intermediately, but solutions of the free ligand of 2AP in these solvents were colorless or pale-yellow. It was furthermore considered that zinc may catalyze the polymerization reaction because 2AP in these solvents was relatively stable but instable in the presence of zinc ion. The 2AP-zinc iodide complex in tetrahydrofuran (THF), chloroform, and methylene chloride (polarity=3~4) was yellow in color and turned red gradually. A sticky dark-red material that adhered to the wall of the beaker was observed due to the poor solubility of the polymer. In non-polar solvents such as pentane, benzene, and diethyl ether, the complex remained a solid powder. The stabilization seemed to happen in relatively non-polar solvents, such as diethyl ether, because precipitation was necessary in order to prevent zinc-mediated polymerization. No precipitate was formed when 2AP (200 µg/mL) was treated with zinc iodide (4 mM) in methylene chloride for 20 hours. A quenching solution (phosphate buffer, 50 mM, pH 7, 0.5 mL) was added to 0.5 mL of sample solution prior to GC analysis, which not only quenched zinc-mediated polymerization but also minimized the chromatographic interference by zinc. The results showed 2AP decayed 70% in 4 hours (FIG. 1) when zinc ion was present. However, when a 2AP/zinc ion solution was treated with the quench solution within 1 minute, 2AP was retained at 97% and maintained stable during a 20 hour period. The results indicated that zinc ion catalyzed the deterioration of 2AP.

EXAMPLE 6

Stability of 2-AP Zinc Iodide Complex

Figure 2:
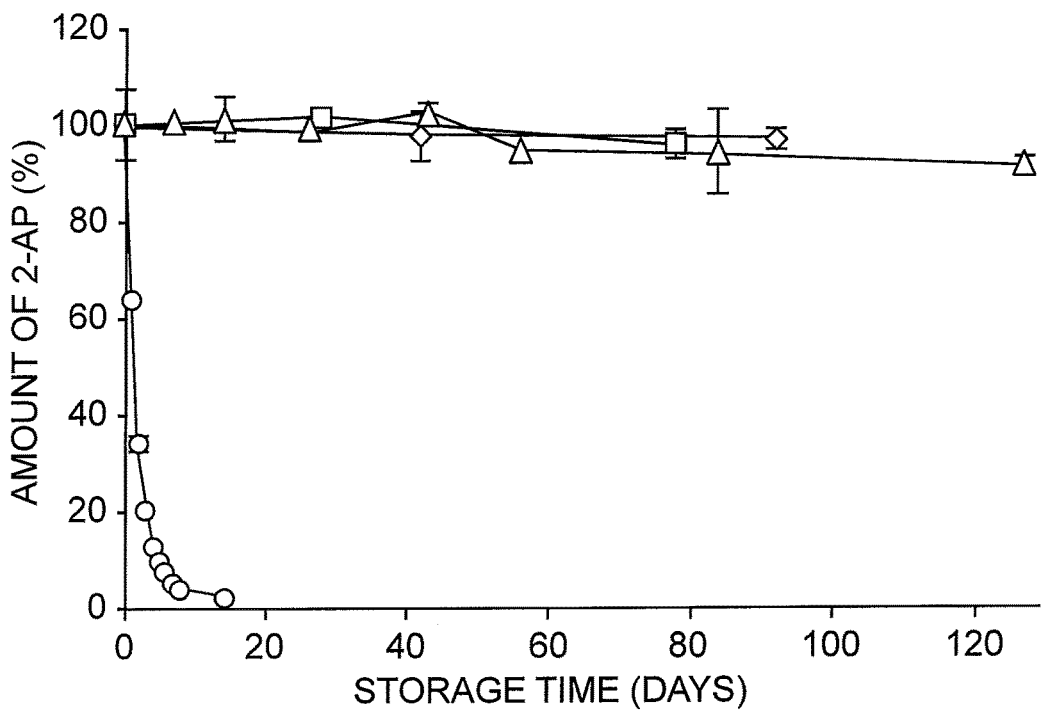
FIG. 2 shows 2-acetyl-1-pyrroline (2-AP) reduction of its zinc iodide complex during storage at −20° C. (diamond, 12.5% 2-AP in complex), 10° C. (square, 14.5% 2-AP in complex), 25° C. (triangle, 14.4% 2-AP in complex) or 10° C. (circle, 0.17% 2-AP in phosphate buffer, 50 mM, pH 7) (mean±SD, n=2).
Figure 3:
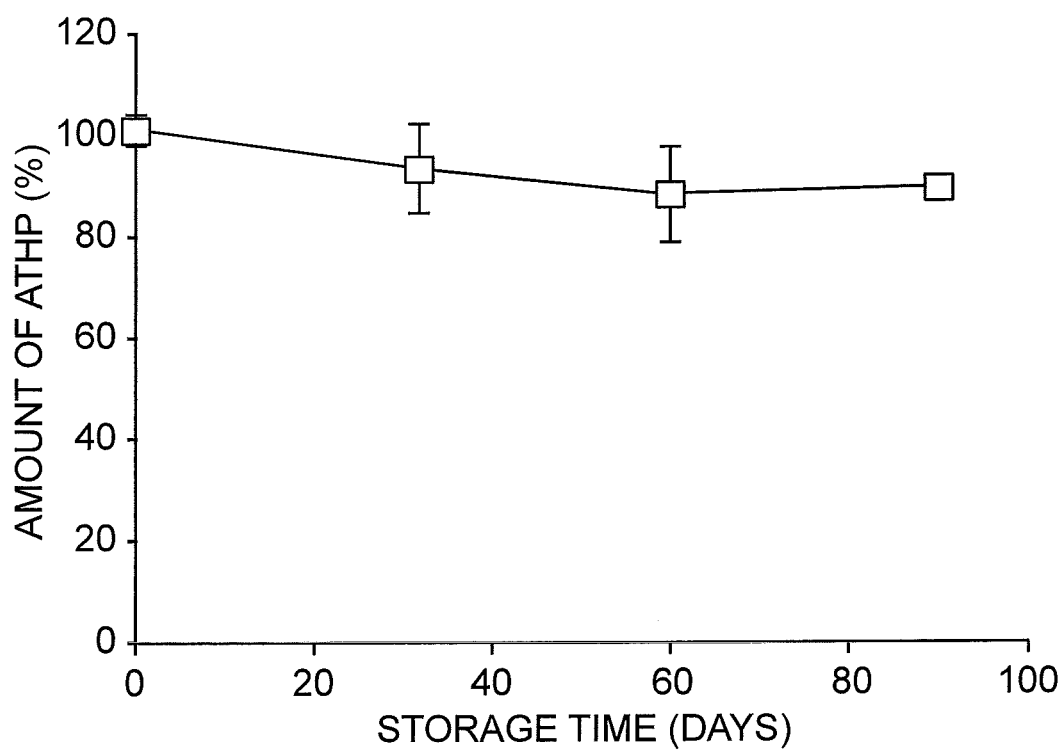
FIG. 3 shows ATHP reduction of its zinc iodide complex stored at 25° C. (mean±SD, n=2).

The tendency of metal-ligand coordination complexes to form can be applied for the protection of unstable compounds, such as the stabilization of 1-pyrroline as a stable crystalline complex with zinc ion (Baxter, et al. (1991) supra; Freer, et al. (1993) *Acta. Cryst.* c49:2115-2117). The stability of 2-AP zinc iodide complex was studied over a period of three months. A 0.17% aqueous solution of 2-AP (pH 7) showed 80% reduction after 3 days and 90% after 5 days. However, 2-AP complex stored at the various temperatures showed significantly increased stability (FIG. 2). Lower temperature storage was found to favor the complex stability. During storage at −20° C., the 2-AP content was maintained at 97% in the complex (content=12.5%) after 92 days of storage (FIG. 2). When the 2-AP complex (14.5%) was stored at 10° C., 96% retention was observed after 78 days of storage. Meanwhile, in a moisture-free environment, 2-AP (14.4% complex) was observed to decline by only 6% after 3 months of storage at 25° C. The ATHP-ZnI$_2$ complex was similarly stable and only 11% of the ATHP was lost after three months of storage at 25° C. under dry conditions (FIG. 3).

What is claimed is:

1. A composition comprising an alkanone-heterocyclic flavorant in complex with a transition metal salt comprising a metal of group 2 to 12 of a periodic table.

2. The composition of claim 1, wherein the alkanone-heterocyclic flavorant has the structure of Formula I:

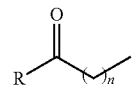

Formula I where R is a heterocyclic group and n is 0 to 20.

3. The composition of claim 2, wherein the alkanone-heterocyclic flavorant has the structure of Formula II, Formula III or Formula IV:

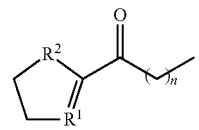

Formula II

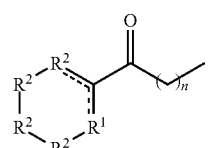

Formula III

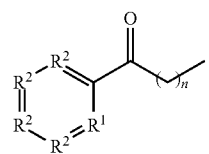

Formula IV wherein n is a number from 0 to 20; $R^1$ is N or S; each $R^2$ is independently N, S, C or O; and dashed lines represent a single or double bond, with the proviso that there is either 0 or 1 double bond.

4. The composition of claim 1, wherein the transition metal salt comprises an iron halide salt, magnesium halide salt, zinc halide salt, or a combination thereof.

5. The composition of claim 4, wherein the zinc halide salt comprises zinc iodide, zinc bromide, zinc chloride, or a combination thereof.

6. A food product or food topping comprising the composition of claim 1.

* * * * *